United States Patent [19]
Wood

[11] Patent Number: 4,562,070
[45] Date of Patent: Dec. 31, 1985

[54] METHOD OF ENHANCEMENT OF PILIATED PHASE OF BORDETELLA BRONCHISEPTICA

[75] Inventor: Sarah W. Wood, Pittsburgh, Pa.

[73] Assignee: Bactex Corporation, Pittsburgh, Pa.

[21] Appl. No.: 528,218

[22] Filed: Aug. 31, 1983

[51] Int. Cl.⁴ .............................................. A61K 39/02
[52] U.S. Cl. ....................................... 424/92; 424/88; 435/253; 435/822
[58] Field of Search ....................... 435/253, 820, 822; 424/88, 92, 93

[56] References Cited

U.S. PATENT DOCUMENTS

| | | | |
|---|---|---|---|
| 3,873,691 | 3/1975 | Kasuga et al. | 424/92 |
| 3,950,512 | 4/1976 | Emery et al. | 424/92 |
| 4,016,253 | 4/1977 | Switzer et al. | 424/92 |
| 4,225,583 | 9/1980 | Switzer et al. | 424/92 |

Primary Examiner—Sam Rosen
Assistant Examiner—William J. Herald
Attorney, Agent, or Firm—Omri M. Behr

[57] ABSTRACT

Organisms of *Bordetella bronchiseptica* which can exist in both piliated and nonpiliated phases can be encouraged to convert into phase stable piliated colonies by reduction of the normal growth temperature and aging of the colonies.

4 Claims, No Drawings

METHOD OF ENHANCEMENT OF PILIATED PHASE OF BORDETELLA BRONCHISEPTICA

BACKGROUND OF THE INVENTION

Many piliated organisms are known. Such organisms exist in colonies which are predominantly piliated (P+ phase) and those which are predominantly non-piliated (P− phase). The colonies of P+ and P− for each species have a fairly distinctive morphology and those have knowledge of such morphology can, with various degrees of effort and difficulty, separate colonies in the P+ from P− phase.

It has further been shown in the case of *P. aeruginosa* (Alan M. Levine, PhD. Thesis, University of Pittsburgh, 1979) that in that organism the growth in a particular environment will tend to equilibrate at ratios which depend upon the initial state of the culture and the rate at which one phase is formed from the other, which rates are affected by growth and the media conditions.

It has further been shown that while both piliated and nonpiliated organisms will grow in certain mammalian hosts, the diseases which these organisms cause in these hosts generally occur only or principally when the P+ phase is present. Correlations are known between the prevalence of P+ in an infecting strain and the virulence of the infection. In designing pilic antigens for vaccine purposes it is therefore desirable to grow organisms producing the largest number of pili whereby either a bacterin or pure pilus vaccine can be isolated.

It has been reported, (Yokomizo and Shimizu, *Res. Vet. Sci.*, 27, 15 (1979)) supported by an initial report by Bemis, et al., (*J. Clin. Microbiol.*, 5, 471 (1977)) that piliated organisms of *B.bronchiseptica* rather than the unpiliated phase are the pathogenic organisms in swine atrophic rhinitis. Bemis, et al. (*J.Clin. Microbiol.*, 15, 1120(1982)) report the preparation of piliated cultures and the separation of the pili therefrom. Heretofore however, there have been no reports on how *B.bronchiseptica* organisms can be encouraged to grow substantially in the piliated phase to produce cultures which are phase stable after several passages. This phase stability is important since many organisms are reported to lose their virulence after a plurality of passages in laboratory growth media as opposed to growth in their natural hosts.

SUMMARY OF THE INVENTION

It has been found that by growing *B.bronchiseptica* on conventional growth media which may be liquid or solid, that is to say, broth or gel, suitably the latter, under normal growth conditions for a short period of time and thereafter cooling the environment of growth and permitting the initial growth to age at that reduced temperature, a wart-like type of growth known as papillae is noted which contains organisms substantially in the piliated phase. Organisms taken from such papillae may then be grown in conventional growth conditions to provide organisms of a high degree of virulence against which a killed cell bacterin (from the same source) offers a very high level of protection. The process is not limited to a particular strain of *B.bronchiseptica* or a particular growth medium.

DESCRIPTION OF THE PREFERRED EMBODIMENTS

Strains of *Bordetella bronchiseptica* which are to be grown in the piliated phase may be grown on any growth medium suitable to the organism. There may be utilized tryptose phosphate broth such as the commercially available dehydrated tryptose phosphate broth which, when diluted, comprises approximately 2% tryptose, 0.2% dextrose, 0.5% sodium chloride and 0.25% disodiumphosphate. This is pH adjusted to approximately pH 7.3 with aqueous sodium hydroxide and autoclaved. While the liquid medium may be employed it is preferred to add 2% agar thereto in order to provide solid medium. Another suitable growth medium is brucella agar (DIFCO Laboratories, Detroit, Mich.)

It is generally preferred that the strains to be grown in the piliated phase are plated out on solid tryptose-phosphate medium and grown at 35°–38° C., suitably at about 37° C. for from about 1 to about 4 days, suitably for about 2 days. The plate is then transferred to a cooler environment preferably an environment of from about 20° to about 27°, suitably 22° to 24° C. for a period of from about 15 to about 20 days. Care should be taken that the medium does not dry out. While heroic measures need not be taken, it has been found suitable to cover the growth plate with a cover plate and the gap between the two, closed by conventional adhesive tape. After 15–20 days small wart-like protruberences appear scattered over the surface of the colony. Growth is allowed to proceed until these warts are large enough to pick with an inoculating loop, transferred to fresh medium and grown at about 37° C. for 48 hours to provide a P+ colony. This colony can be readily distinguished in appearance since it is large and flat with a rough matt-appearing surface. This is contrasted to the P− colony which is small compact and convex and has a shiny glistening appearance. When prepared in the above manner the colonies are phase stable after freeze-thaw cycling and numerous lab passages. The organisms are suitably grown in tryptose phosphate agar broth in the usual manner, growth in the 100 to 1,000 liter scale continues for 18 to 30 hours, after which time the fermentation vessel is inactivated by the addition aqueous formaldehyde. A final concentration of between 0.1 and 0.3, suitably about 0.2% of 37% by weight of formaldehyde is suitable. The product to be used as a vaccine need not be further adjusted in any way.

In virulence test results a nonpiliated strain of *B.bronchiseptica* was scored against a piliated colony from the same source. In a test of 12 pigs the NTAS (nasal turbinate atrophy score) was 0.49 whereas with 41 animals tested with the piliated strain a score of 1.975 was obtained indicating a 4 to 5 fold increase in virulence of the piliated over the nonpiliated form of the same strain.

Conversely the piliated *B.bronchiseptica* bacterin provided more significant protection against a more severe laboratory challenge (score of 1.76 for the new challenge v. 0.86 for the old challenge).

EXAMPLE 1

Production of Piliated Colonies of *B.Bronchiseptica*

Growth medium used for obtaining piliated clones of *Bordetella bronchiseptica*.

| Tryptose Phosphate Broth (T-P Broth) | |
| --- | --- |
| tryptose | 20 gm |
| dextrose | 2 gm |
| sodium chloride | 5 gm |
| disodium chloride | 2.5 gm |
| deionized water | 1 liter |
| Agar | 20 gm |

Adjust pH from 7.0 to 7.3 with 40% NaOH solution if necessary. Autoclave at minimum of 15 psi (121° C.): 1–3 liters for 30 min., 15 liters for at least 45 min, and 30 liters for at least 1 hour. (Add 20 gm agar for solid media.)

Growth Conditions: Strains of B.bronchiseptica were plated out on solid T-P medium obtained as above, grown first at 37° for 2 days, then transferred to 23° and held for an additional 20 days. Care was taken to insure the medium does not dry out (by taping the plate shut). After about 15–20 days (variable), small protuberances appear scattered over the surface of a colony, like warts. These are allowed to grow large enough to pick with an innoculating loop, then transferred to fresh medium and grown at 37° C. for 48 hours. A characteristic colony type was obtained that correlates with presence of pili in the Electron Microscope. The P+ colony morphology is large and flat compared to P−, which is small, compact, and convex. In addition, P+ colony surface is rough and matte (like beaten metal) compared to P−, which is very shiny and glistening. These features may be related to presence or absence of capsular antigens, but so far they have correlated with piliation. The P+ colony type may have a flat spreading border, depending on wetness of the agar and incubation times; P− has a sharply defined border that does not spread out from the main body of the colony even after several days growth.

These two colony types are relatively stable and are easily distinguished. They are stable after one freeze-thaw cycle and after numerous consecutive lab passages.

EXAMPLE II

Production of B.bronchiseptica Vaccine

The organisms are seeded from a source as above in Example I and grown in the same medium without agar. Strains of B.bronchiseptica-B were plated out on solid T-P medium obtained as above.

Stock cultures are grown in 300 to 500 ml resistant pyrex glass flasks, subseed cultures are grown in 300 to 500 ml resistant glass flasks and 4-liter resistant glass jugs.

Production seeds are grown in 20-liter resistant glass jugs. Production cultures are grown in 48-liter resistant glass jugs.

Stock seed is prepared by reconstituting master seed into medium as described above. The culture is grown for 24 to 48 hours at 35° to 37° C. The cultures are evaluated for purity (Gram Stain), cell morphology. The culture is then mixed with an equal volume of milk stabilizer which is desiccated and stored at 35° to 45° F.

Technique of Inoculation

1. Subseed 1:

Flasks of 300 to 500 ml capacity containing 100 to 200 ml of medium are inoculated by means of a sterile pipette or syringe with 1–3 ml of reconstituted stock seed which has been determined as acceptable. Adequate growth is determined by visual examination.

2. Subseed 2:

Flasks of 4-liter capacity containing 1.5 to 2 liters of medium are inoculated with 10% inoculum by volume from Subseed 1 using aseptic technique. This culture is incubated at 35° to 37° C. for 18 to 30 hours. Adequate growth is determined by visual observation.

3. Production Seed:

Glass jugs of 20 liter capacity containing 15 liters of medium are inoculated, by means of sterile transfer station, with 5% to 10% inoculum from Subseed 2 using aseptic technique. Production seed is incubated aerobically at 35° to 37° C. for 16 to 24 hours. Adequate growth is determined by visual observation.

4. Production Culture:

Glass jugs of 48-liter capacity containing 30 liters of medium are inoculated using aseptic technique by means of a sterile transfer station with 5% to 10% inoculum of satisfactory production seed. Production cultures are incubated at 35° to 37° C. for 18 to 30 hours.

All phases of incubation are at 35° to 37° C. for 16 to 30 hours. The medium is agitated throughout the incubation period by the injection of sterile filtered air (sparging) and/or by use of magnetic stirrers or similar stirring devices. Three to 8 ml of sterile antifoam per liter of culture are aseptically added to each seed or production culture jug.

Growth is observed visually during the incubation period of all seed and production cultures. Upon observation of a very heavy suspension of growth, a sample of culture is taken and used to determine the nephelometry value (in the case of production culture). Purity is tested by Gram stain.

When it has been determined by cell counts, nephelometry and/or other evaluation methods that sufficient growth has occurred, the production jugs are harvested or inactivated in situ.

Preparation of the Vaccine

Inactivation of the product is accomplished by the addition of formaldehyde solution to a final concentration not to exceed 0.2%. The product is inactivated in production vessels and incubated at 35° to 37° C. for 48 hours. The pH of the product is adjusted to 7.3 to 7.8 with 0.5N HCl solution.

At the end of the inactivation period the product is tested for the presence of viable Bordetella bronchiseptica organism by inoculating a 10 ml sample into 400 ml of tryptose broth, incubating at 34° to 37° C. for 14 days, and observing for macroscopic evidence of microbial growth. Any growth will be confirmed by gram stain.

Assembly of Units to Make a Serial

A typical serial may be formulated as follows:

| | |
| --- | --- |
| Acceptable B. bronchiseptica Harvest Material | 360,000 ml |
| Aluminum Hydroxide Suspension, Serile | 240,000 ml |
| 0.5N Hydrochloric Acid Solution | 100 ml |
| Gentamicin | 165 ml |
| 37% Formaldehyde | 800 ml |
| | 601,065 ml |

The serials are packaged to provide vials containing 50 or 125 doses at 1 ml per dose.

EXAMPLE III

Administration and Dosage

The vial is shaken well before use. Injected subcutanesously using aseptic technique according to the following dosage schedule:

Sows/Gilts:
- 1 ml at time of breeding
- 1 ml 7 to 14 days prior to first farrowing
- 1 ml 7 to 14 days prior to each subsequent farrowing Newborn:
- 1 ml at 7 days of age
- 1 ml between 17 and 28 days of age

I claim:

1. A process for enhancing a prevalence of phase stable colonies of the piliated phase of *Bordetella bronchiseptica* which comprises growing organisms from a source selected from the group consisting of piliated organisms, unpiliated organisms and mixtures thereof on a growth medium suitable for growth of said organisms at a temperature of 35° to 38° C. for 1 to 4 days, reducing the environmental temperature to between 20° and 27° C. for from about 15 to about 20 days until papillae are noted.

2. A process in accordance with claim 1 wherein the growth medium is tryptose phosphate broth, tryptose phosphate agar or brucella agar.

3. A process in accordance with claim 1 wherein the organism is initially grown at about 37° C. for about 2 days and held at about 23° C. for 15-20 days.

4. A vaccine composition comprising formaldehyde treated cells grown from colonies prepared in accordance with the process of claim 1.

* * * * *